US00PP30620P2

(12) United States Plant Patent
Kleinwee

(10) Patent No.: US PP30,620 P2
(45) Date of Patent: Jun. 25, 2019

(54) ***LOBELIA* PLANT NAMED 'LOBZ0015'**

(50) Latin Name: *Lobelia erinus*
Varietal Denomination: LOBZ0015

(71) Applicant: SYNGENTA PARTICIPATIONS AG, Basel (CH)

(72) Inventor: Theodorus Cornelis Maria van Kleinwee, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/932,675

(22) Filed: Apr. 6, 2018

(30) Foreign Application Priority Data

Dec. 22, 2017 (QZ) ..... PBR 2017/3391

(51) Int. Cl.
*A01H 5/02* (2018.01)
*A01H 6/26* (2018.01)

(52) U.S. Cl.
USPC ..... Plt./451

(58) Field of Classification Search
USPC ..... Plt./451
See application file for complete search history.

*Primary Examiner* — Susan McCormick Ewoldt
(74) *Attorney, Agent, or Firm* — Dale Skalla

(57) ABSTRACT

A new *Lobelia* plant named 'LOBZ0015' particularly distinguished by its medium sized, deep blue flowers, medium green foliage, very good branching and a mounding to semi-trailing plant habit.

1 Drawing Sheet

Latin name of the genus and species of the plant claimed: *Lobelia erinus.*

Varietal denomination: 'LOBZ0015'.

BACKGROUND OF THE NEW PLANT

The present invention comprises a new and distinct cultivar of *Lobelia*, botanically known as *Lobelia erinus* and hereinafter referred to by the cultivar name 'LOBZ0015'.

'LOBZ0015' is a product of a planned breeding program. The new cultivar has medium sized, deep blue flowers, medium green foliage, very good branching and a mounding to semi-trailing plant habit.

The seed from which the variety was grown originates from an open pollination made on the open field in the summer of 2012, The Netherlands.

The female parent was an offspring of the commercial variety 'Blue Lagoon'. A group of plants of this variety was grown in 2011, open pollinated, and seed was bulk harvested. A group of plants derived from these seeds, varying in flower color from white to deep blue, were planted on the field in summer 2012, open pollinated, and seed was bulk harvested. Specific characteristics of the female parent are, therefore, not known.

The male parent of 'LOBZ0015' is unknown, as the cross from which the variety originates was an open pollination.

The resulting seeds were sown in May 2013 and 'LOBZ0015' was selected as one flowering plant within the progeny of the stated cross in September 2013 in a controlled environment in Andijk, The Netherlands.

The first act of asexual reproduction of 'LOBZ0015' was accomplished when vegetative cuttings were propagated from the initial selection in the fall of 2013 in a controlled environment in Andijk, The Netherlands.

BRIEF SUMMARY OF THE INVENTION

Horticultural examination of plants grown from cuttings of the plant initiated in the spring of 2014 in Andijk, The Netherlands, and continuing thereafter, has demonstrated that the combination of characteristics as herein disclosed for 'LOBZ0015' are firmly fixed and are retained through successive generations of asexual reproduction.

'LOBZ0015' has not been observed under all possible environmental conditions. The phenotype may vary significantly with variations in environment such as temperature, light intensity and day length.

A Plant Breeder's Right for this cultivar was applied for in the European Union on Dec. 22, 2017, No. 2017/3391. 'LOBZ0015' has not been made publicly available prior to the effective filing date of this application, notwithstanding any disclosure that may have been made less than one year prior to the effective filing date of this application by the inventor or another who obtained 'LOBZ0015' directly from the inventor.

The following traits have been repeatedly observed and are determined to be basic characteristics of the new variety. The combination of these characteristics distinguishes this *Lobelia* as a new and distinct variety.

DESCRIPTION OF THE PHOTOGRAPHS

Figure 1:
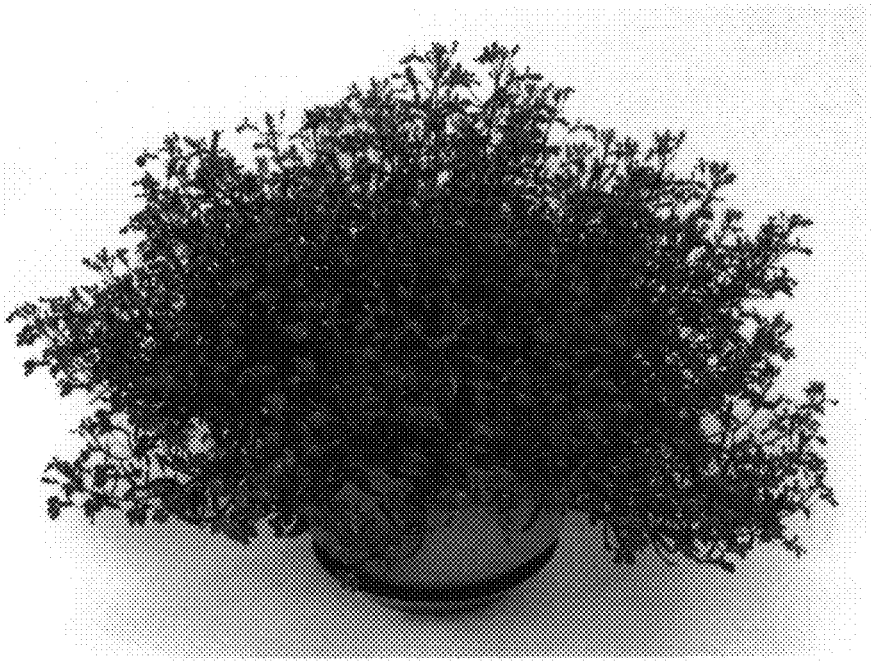
Figure 2:
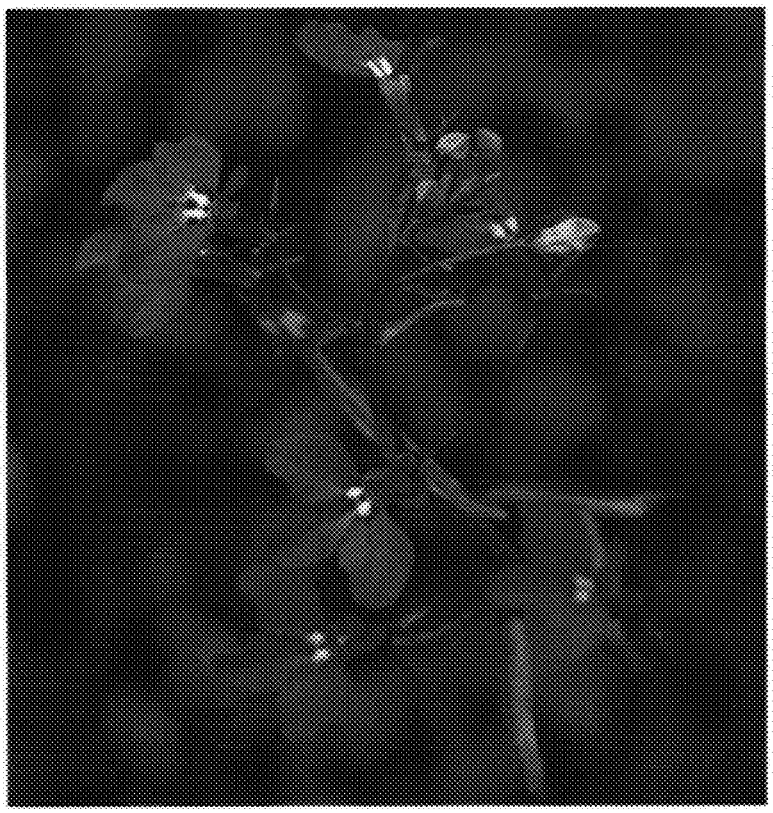

The accompanying photograph drawings show typical flower and foliage characteristics of 'LOBZ0015' with colors being as true as possible with an illustration of this type. The photograph drawings show in FIG. 1 a flowering potted plant of the new variety and in FIG. 2 a close-up of its flowers.

DETAILED BOTANICAL DESCRIPTION

The aforementioned photographs were taken in September 2017 from plants grown in an outdoor trial in Andijk, The Netherlands. These plants were grown in containers and were approximately 17 weeks of age. The close-up photograph was taken at the same time.

The measurements were taken in Andijk, The Netherlands in September 2017 on 17 week old plants that were grown outside in containers. Culture of these plants had started in week 21, 2017 with planting of rooted, non-pinched cuttings.

Color chart used: The Royal Horticultural Society Colour Chart (R.H.S.), 2001.

TABLE 1

DIFFERENCES BETWEEN THE NEW VARIETY 'LOBZ0015' AND A SIMILAR VARIETY

| | 'LOBZ0015' | 'TECH DARBULE' (U.S. Plant Pat. No. 20,681) |
|---|---|---|
| Flower color: | Deeper blue than 'Tech Darbule' | Deep blue |
| Plant vigor: | medium | Strong |
| Plant habit: | Mounding to semi-trailing | Semi-trailing |

Plant:

*Growth and habit.*—Medium vigorous growth habit; dense and freely branched with mounding to semi-trailing plant habit.

*Height.*—15 cm.

*Height (inflorescence included).*—About 20 cm.

*Width.*—35 cm.

*Branching characteristics.*—6 main stems, each with 4 to 5 secondary branches.

*Crop time to flowering, response time to produce a finished flowering plant.*—About 12 weeks for a 12 cm pot.

*Garden performance.*—Used as patio planters, in mixed container plantings, or in garden beds.

*Time to initiate and develop roots.*—14-20 days at 22° C.

*Root description.*—Fibrous and freely branching.

Stem:

*Characteristics.*—Triangular stem shape, branches of the flowers are developed at almost every node.

*Stem length.*—9-10 cm.

*Diameter.*—0.3 cm.

*Internode length.*—1.7-3.0 cm.

*Color.*—RHS 146A in old stem RHS 144A when young.

*Texture.*—Smooth.

Foliage:

*Arrangement.*—Alternate.

*Shape.*—Lanceolate.

*Apex.*—Abruptly acute.

*Base.*—Attenuate.

*Margin.*—Entire to slightly incised.

*Leaf length.*—1.5-4 cm.

*Leaf width.*—0.3-1.4 cm.

*Immature leaf, color upper surface.*—RHS 144A.

*Immature leaf, color lower surface.*—RHS 144A.

*Mature color upper surface.*—RHS 137A.

*Mature color lower surface.*—RHS 137C.

*Venation type.*—Pinnate.

*Venation color, upper surface.*—RHS 137A; slightly lighter.

*Venation color, lower surface.*—RHS 137A; slightly lighter.

*Texture.*—Smooth, occasionally a hair.

*Petiole.*—Attached to stem, sessile no petiole.

Inflorescence:

*Type of inflorescence.*—Raceme, composed of single flowers in an alternate arrangement with one flower per node, subtended by a small leaflet.

*Blooming habit.*—Continuous through the growing season from spring to the fall.

*Quantity of inflorescences per plant.*—About 200.

*Quantity of flowers per inflorescence.*—Up to 4 open flowers, and additional buds.

*Lastingness of individual blooms on the plant.*—3-6 days, depending on temperature.

*Fragrance.*—None.

*Inflorescence length.*—10 cm.

Peduncle:

*Color.*—RHS 143A-RHS 144A.

*Length.*—7-8 cm.

*Diameter.*—0.2 cm.

*Texture.*—Pubescent.

Pedicels:

*Color.*—RHS 143A.

*Length.*—2-3 cm.

*Diameter.*—0.1 cm.

*Texture.*—Smooth, only occasionally a hair.

Flower:

*Corolla type and shape.*—Single, zygomorphic; upper lip is formed by two small petals, lower lip has three larger petals; petals are fused at the base forming a relatively long funnel-shaped tube.

Immature flower:

*Main color upper surface.*—RHS 89B.

*Main color lower surface.*—RHS N89 at top. Whiter than RHS N155A at base.

*Immature flower, width.*—1.8 cm.

Mature flower:

*Flower, (horizontal) length.*—2.1 cm.

*Flower, (horizontal) width.*—2.3 cm.

*Flower, vertical length (depth).*—1.5 cm.

*Color upper lip, upper surface.*—RHS N89B.

*Color upper lip, lower surface.*—(Lighter than) RHS N89D.

*Upper petal lobes, length (from the tube opening).*—0.7 cm.

*Upper petal lobes, width.*—Up to 0.3 cm at widest point.

*Color lower lip, upper surface.*—RHS N81A at top and RHS N89B towards base.

*Color lower lip, lower surface.*—RHS N82B.

*Nectaries at base of lower petals.*—Darker than N89A.

*Lower petal lobos, length (from the corolla opening).*—1.2 cm.

*Lower petal lobes, width.*—0.6 cm.

*Tube, color (outside).*—RHS 83D.

*Tube length.*—0.5 cm.

*Tube width.*—0.2 cm.

Petal (lobes):

*Shape.*—Obovate.

*Apex.*—Mucronulate.

*Base.*—Fused.

*Margin.*—Entire.

*Texture upper surface.*—Glabrous

*Texture lower surface.*—Short hair, mainly along the mid vein.

Flower bud:

*Shape.*—Elongate.

*Length.*—0.6 cm.

*Diameter.*—0.2-0.3 cm.
*Color* (*at tight bud*).—Base RHS 157B dark purple RHS N79B toward top.

Calyx:
*Shape.*—3 big leafs 2 smaller ones.
*Sepal color*.—RHS 187A.
*Sepal length* (*fee ends*).—0.9 cm.
*Width.*—0.2 cm, 0.2 cm wider towards top.
*Shape*.—Ligulate.
*Apex*.—Acute.
*Base*.—Fused.
*Texture*.—Pubescent.

Reproductive organs:

Stamens:
*Quantity.*—5.
*Filament, color*.—RHS N88A (Violet group).
*Filament length.*—0.6 cm.
*Filament, diameter.*—0.1 cm.
*Anther color*.—RHS 202B.
*Anther length.*—0.2 cm.
*Pollen amount*.—Few.
*Pollen color.*—3 B-C.

Pistil:
*Quantity per flower.*—1.
*Length.*—0.9 cm.
*Stigma color*.—RHS 155 A.
*Stigma length.*—0.3 cm.
*Style color*.—RHS 90A.
*Style length.*—0.7 cm.

Fruit and seed set: Yes, some seed development observed in the trial Fields.

Disease and insect resistance: Resistance and susceptibility typical for the species, no special observations made.

What is claimed is:

1. A new and distinct cultivar of *Lobelia* plant named 'LOBZ0015' substantially as shown and described herein.

* * * * *